(12) United States Patent
Sasaki

(10) Patent No.: US 9,743,910 B2
(45) Date of Patent: Aug. 29, 2017

(54) ULTRASONIC DIAGNOSTIC APPARATUS, ULTRASONIC IMAGE PROCESSING APPARATUS, MEDICAL IMAGE DIAGNOSTIC APPARATUS, AND MEDICAL IMAGE PROCESSING APPARATUS

(71) Applicant: Toshiba Medical Systems Corporation, Otawara-shi (JP)

(72) Inventor: Takuya Sasaki, Nasu-gun (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 260 days.

(21) Appl. No.: 13/871,463

(22) Filed: Apr. 26, 2013

(65) Prior Publication Data
US 2013/0237825 A1  Sep. 12, 2013

Related U.S. Application Data

(63) Continuation of application No. PCT/JP2011/074684, filed on Oct. 26, 2011.

(30) Foreign Application Priority Data

Oct. 26, 2010 (JP) .................................. 2010-240112

(51) Int. Cl.
*A61B 8/00* (2006.01)
*A61B 8/08* (2006.01)
(Continued)

(52) U.S. Cl.
CPC .......... *A61B 8/5269* (2013.01); *A61B 8/0883* (2013.01); *A61B 8/14* (2013.01);
(Continued)

(58) Field of Classification Search
CPC .......... A61B 8/06; A61B 8/0883; A61B 8/14; A61B 8/466; A61B 8/483; A61B 8/5269;
(Continued)

(56) References Cited

U.S. PATENT DOCUMENTS 4,662,380 A * 5/1987 Riley .......................... 600/443
4,868,651 A * 9/1989 Chou et al. ................ 378/98.7
(Continued)

FOREIGN PATENT DOCUMENTS

EP  0 220 631 A1  5/1987
EP  0 544 328 A2  6/1993
(Continued)

OTHER PUBLICATIONS

Hazewinkel, Michiel, ed. (2001), "Point of inflection", Encyclopedia of Mathematics, Springer, ISBN 978-1-55608-010-4, http://www.encyclopediaofmath.org/index.php?title=Point_of_inflection&oldid=14389.*

(Continued)

*Primary Examiner* — Amanda Lauritzen Moher
(74) *Attorney, Agent, or Firm* — Oblon, McClelland, Maier & Neustadt, L.L.P.

(57) ABSTRACT

According to one embodiment, an ultrasonic diagnostic apparatus according to one embodiment transmits an ultrasonic wave into a predetermined region including a diagnosis target of an object, receives a reflected wave from the predetermined region, and acquires ultrasonic image data based on the reflected wave and comprises a correction unit which executes tone correction of the ultrasonic image data, and in the tone correction, the correction unit calculates a histogram associated with brightness of the image data and calculates a brightness distribution range corresponding to the diagnosis target and a tone correction function using the histogram.

28 Claims, 18 Drawing Sheets

(51) Int. Cl.
  *G06T 5/00* (2006.01)
  *G06T 5/40* (2006.01)
  *A61B 8/14* (2006.01)
  *A61B 8/06* (2006.01)

(52) U.S. Cl.
  CPC ............... *G06T 5/009* (2013.01); *G06T 5/40* (2013.01); *A61B 8/06* (2013.01); *A61B 8/466* (2013.01); *A61B 8/483* (2013.01); *G06T 2207/10132* (2013.01); *G06T 2207/20008* (2013.01); *G06T 2207/30044* (2013.01)

(58) Field of Classification Search
  CPC . G06T 2207/10132; G06T 2207/20008; G06T 2207/30044; G06T 5/009; G06T 5/40
  USPC ........................................................ 600/443
  See application file for complete search history.

(56) References Cited

U.S. PATENT DOCUMENTS

| | | | |
|---|---|---|---|
| 5,469,850 A | 11/1995 | Iizuka et al. | |
| 5,579,768 A * | 12/1996 | Klesenski | G01S 7/52033 600/442 |
| 7,586,653 B2 * | 9/2009 | Pulsifer | G06T 5/009 358/401 |
| 7,676,091 B2 * | 3/2010 | Zwirn | G06T 5/40 382/182 |
| 8,526,729 B2 * | 9/2013 | Mitsunaga | H04N 1/6027 382/167 |
| 9,390,485 B2 * | 7/2016 | Nakamura | G06T 5/004 |
| 2003/0144592 A1 * | 7/2003 | Jeong et al. | 600/438 |
| 2006/0078182 A1 * | 4/2006 | Zwirn | G06T 7/0012 382/128 |
| 2006/0079777 A1 * | 4/2006 | Karasawa | A61B 8/14 600/443 |
| 2008/0130964 A1 * | 6/2008 | Zwirn | G06T 5/40 382/128 |
| 2009/0279764 A1 | 11/2009 | Kaji et al. | |
| 2010/0157161 A1 | 6/2010 | Tanahashi | |

FOREIGN PATENT DOCUMENTS

| | | |
|---|---|---|
| EP | 2 031 873 A2 | 3/2009 |
| JP | 2002-209891 | 7/2002 |
| JP | 2005-103007 | 4/2005 |
| JP | 2005-169155 | 6/2005 |
| JP | 2007-014525 | 1/2007 |
| JP | 2007-117351 | 5/2007 |

OTHER PUBLICATIONS

G Zwirn et al. "A histogram-based technique for echocardiographic image enhancement." Computers in Cardiology 2004; 31: 81-84.*
Extended European Search Report issued Jul. 30, 2015 in Patent Application No. 11836344.9.
International Preliminary Report on Patentability issued May 16, 2013 in PCT/JP2011/074684 filed Oct. 26, 2011.
Written Opinion issued Dec. 20, 2010 in PCT/JP2011/074684 filed Oct. 26, 2011 submitting English language translation only.
International Search Report mailed Dec. 20, 2011, in PCT/JP2011/074684 filed Oct. 26, 2011 (with English Translation).
International Written Opinion mailed Dec. 20, 2011, in PCT/JP2011/074684 filed Oct. 26, 2011.

* cited by examiner

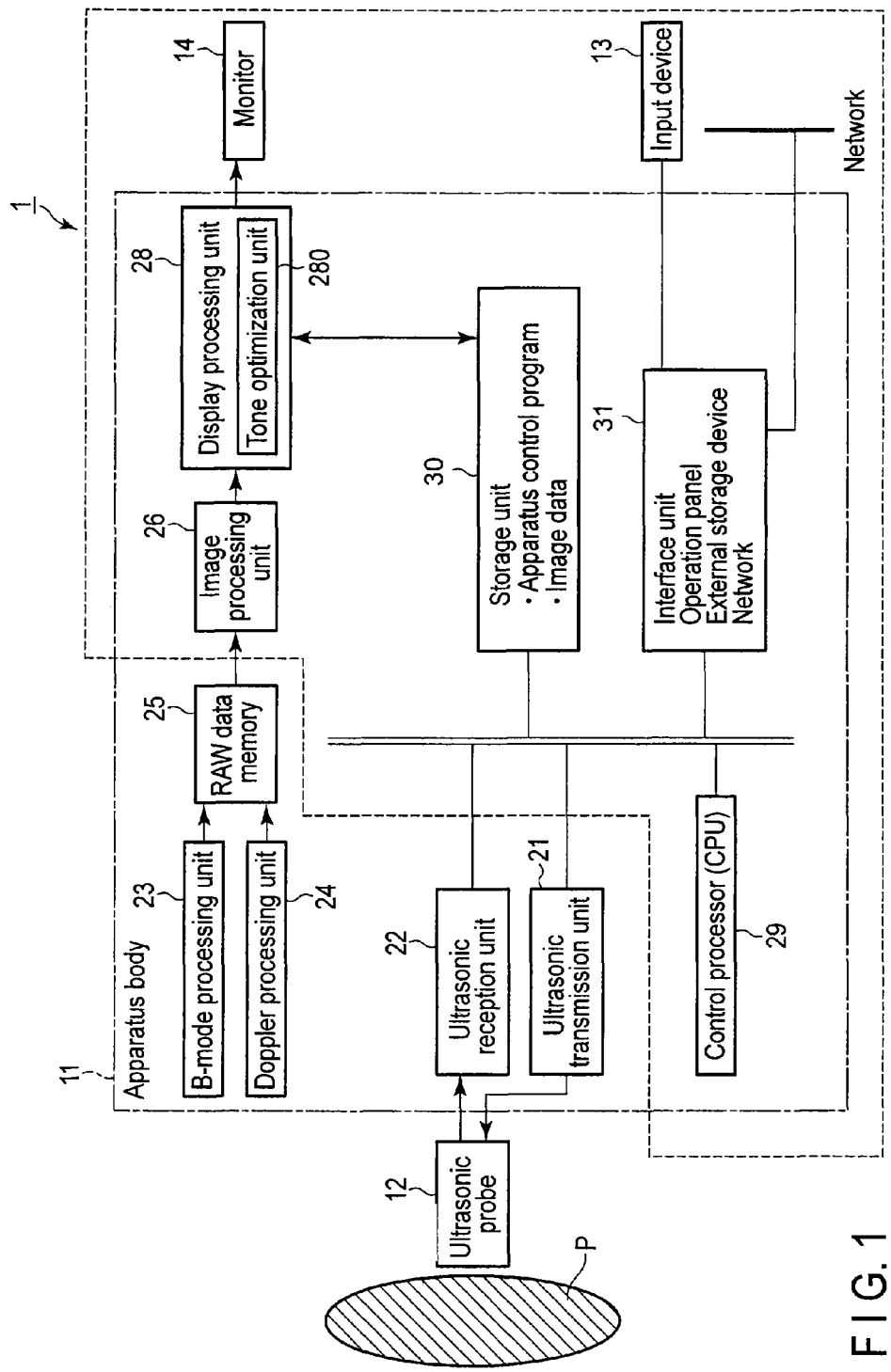
F I G. 1

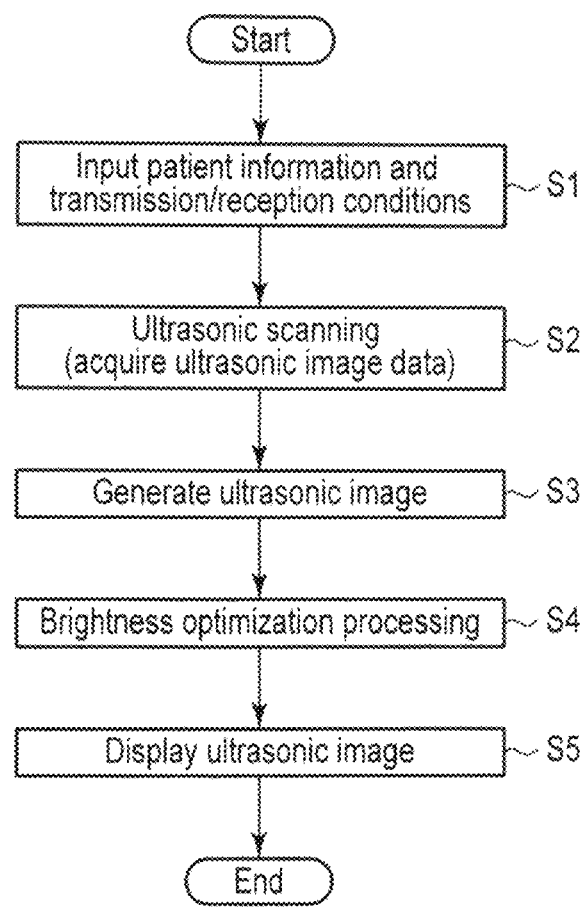
F I G. 2

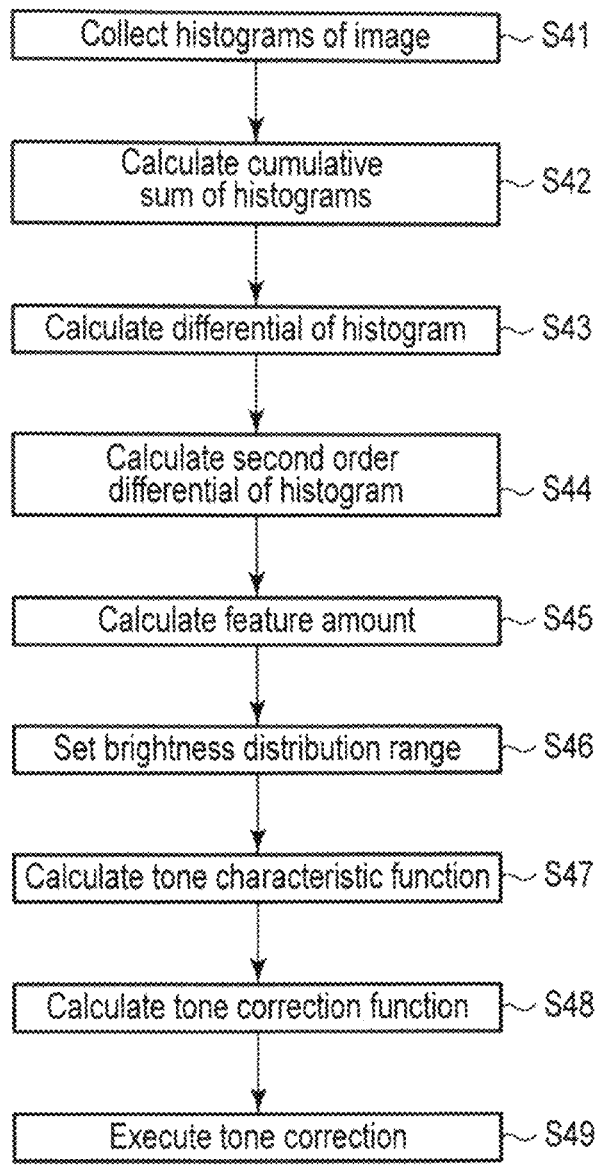
F I G. 3

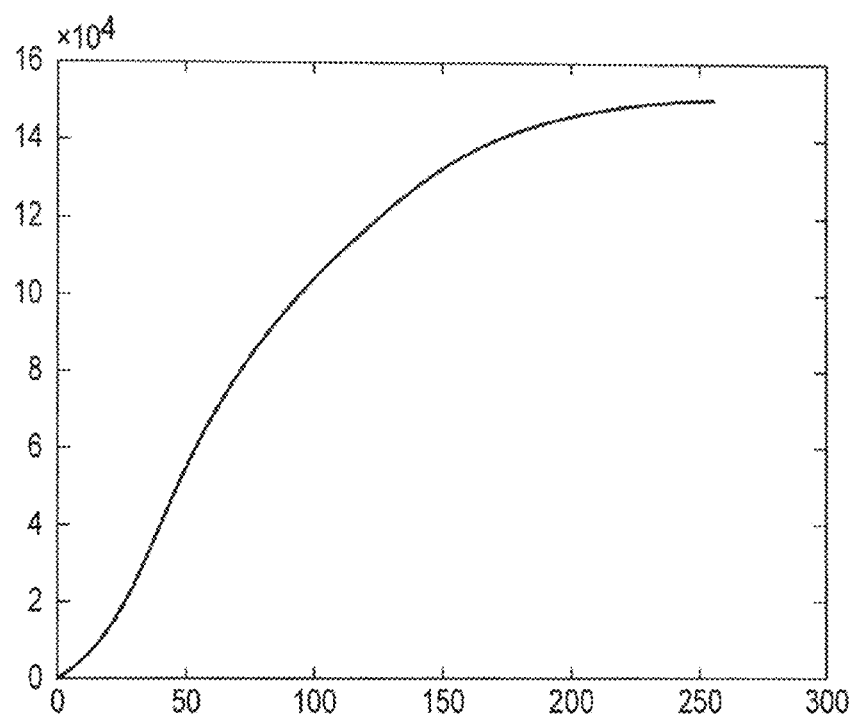
F I G. 12
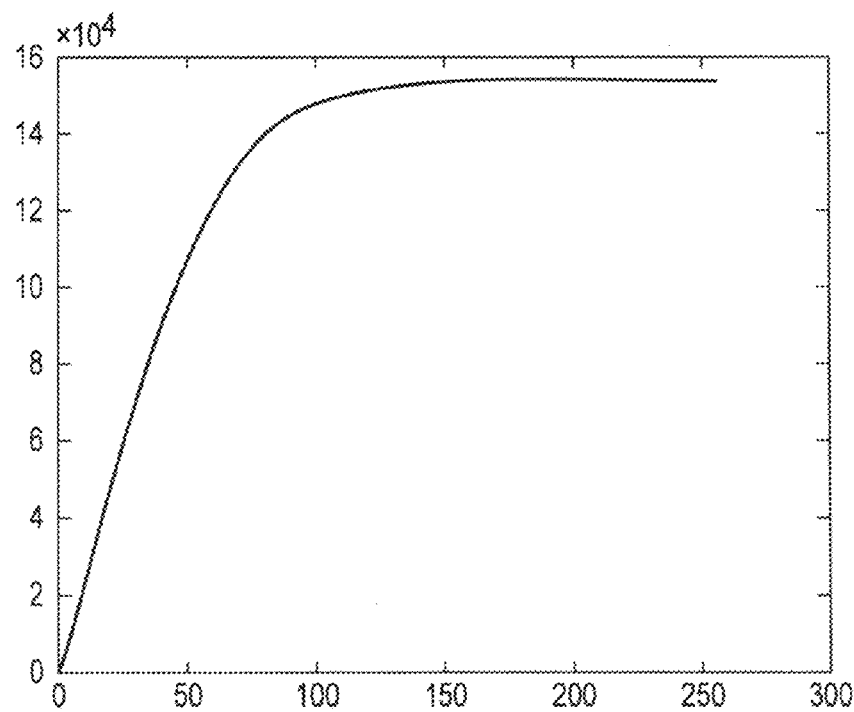
F I G. 13

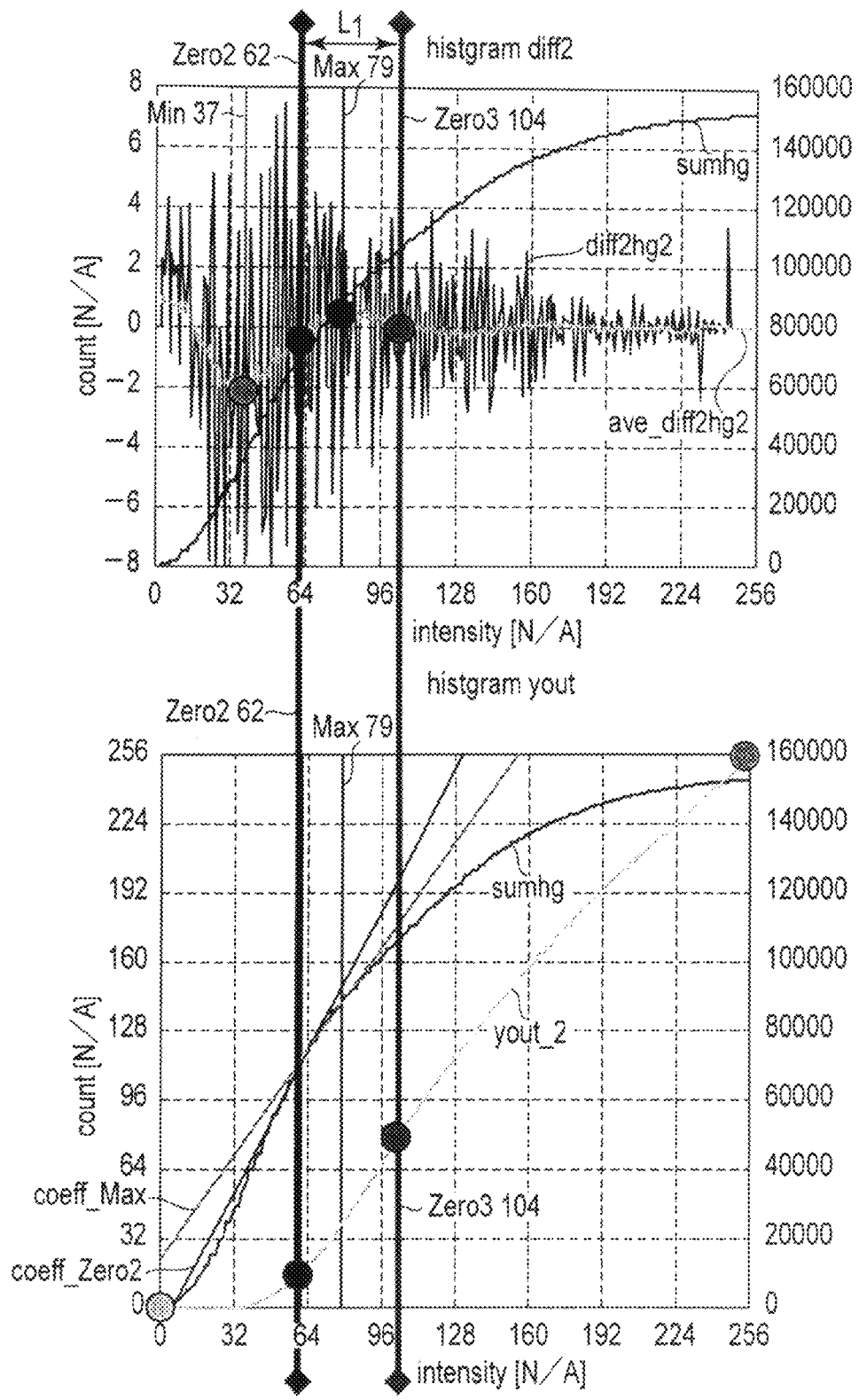
F I G. 14

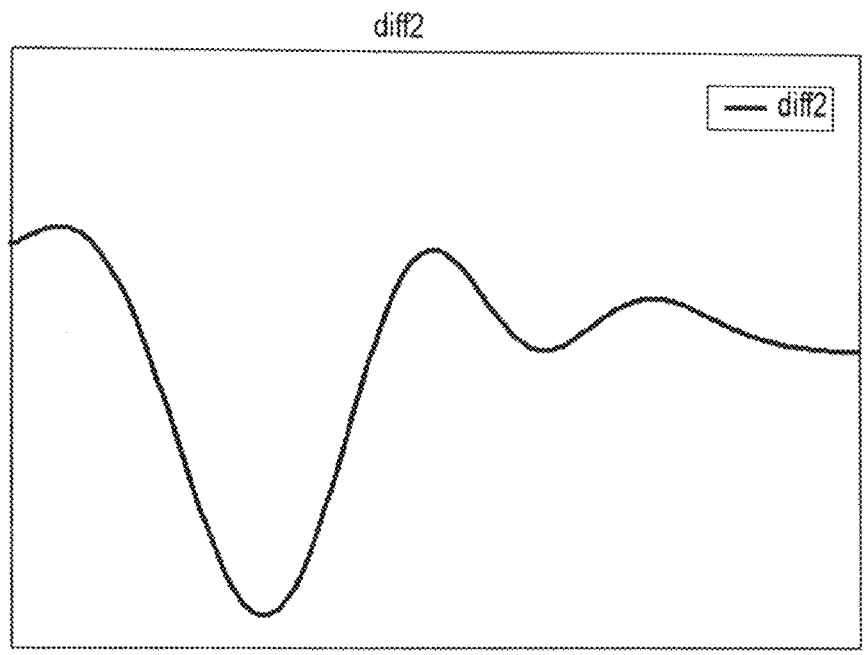
F I G. 18
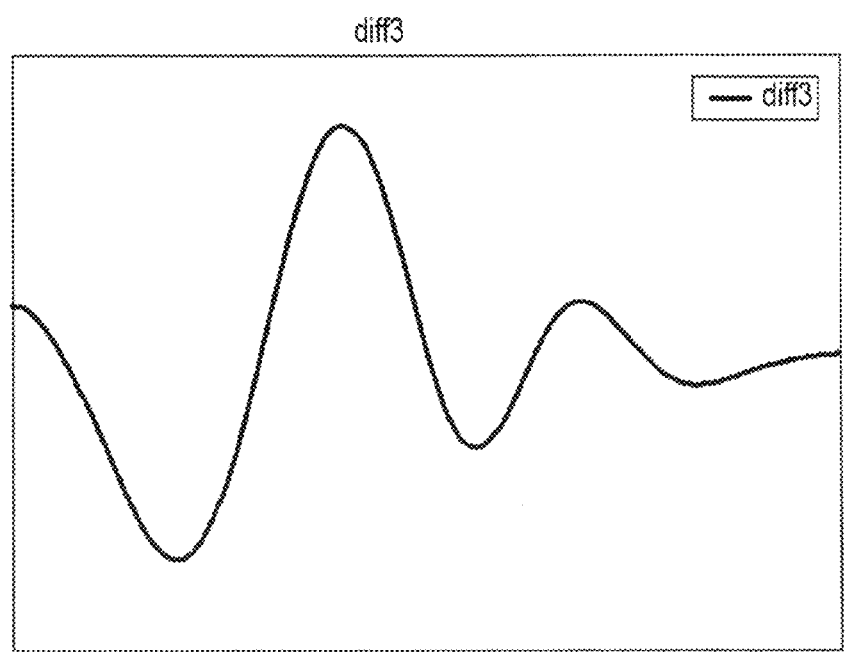
F I G. 19

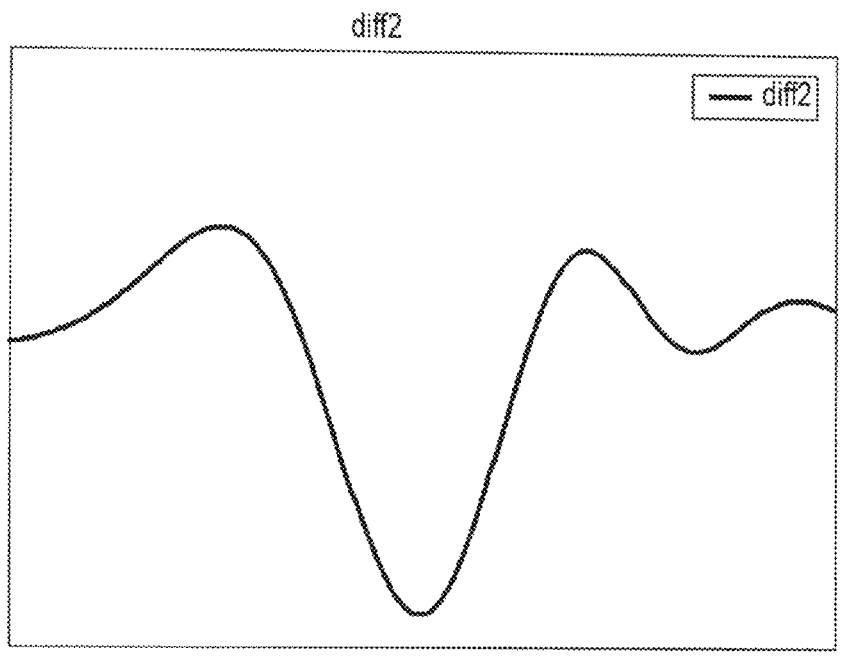
F I G. 22
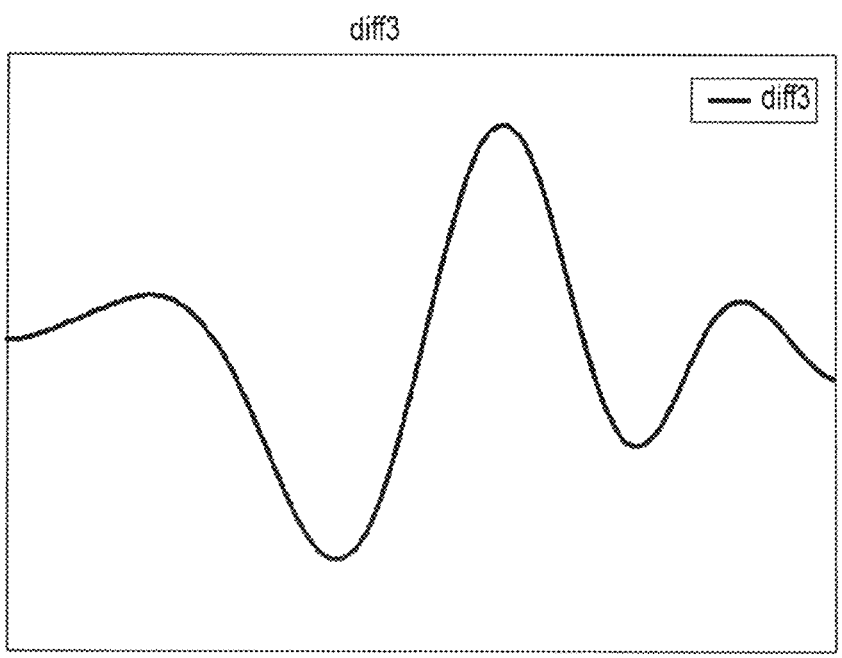
F I G. 23

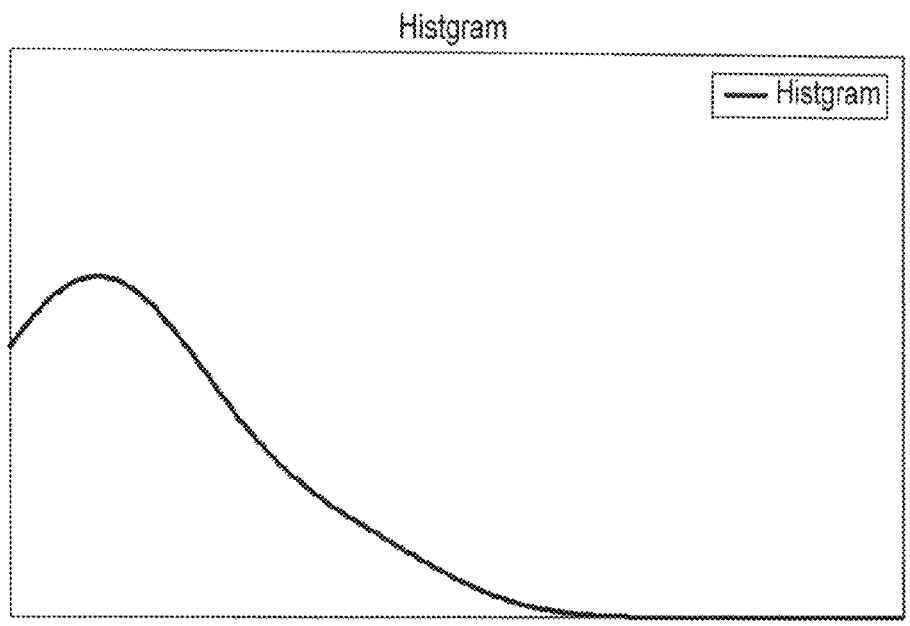
F I G. 24
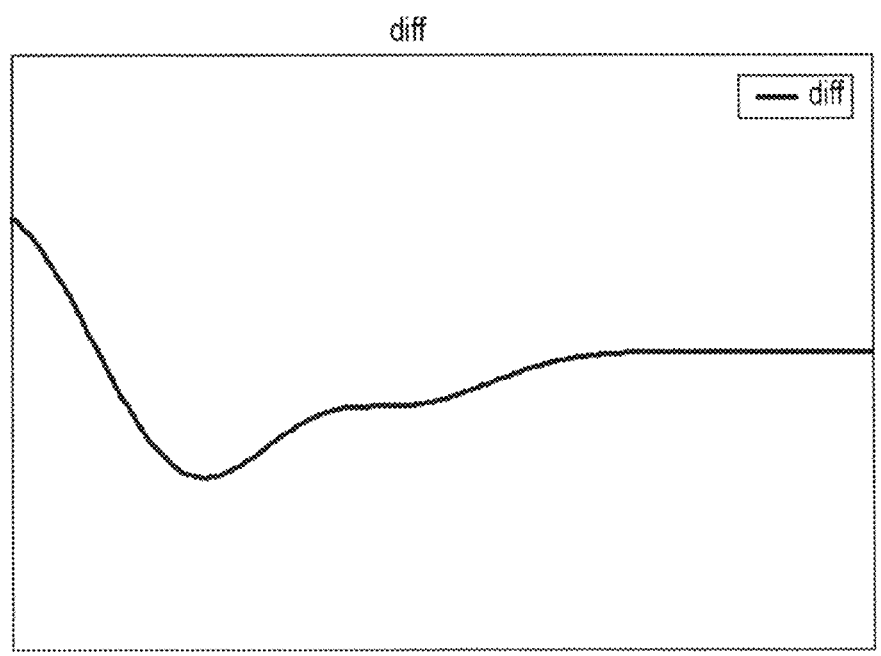
F I G. 25

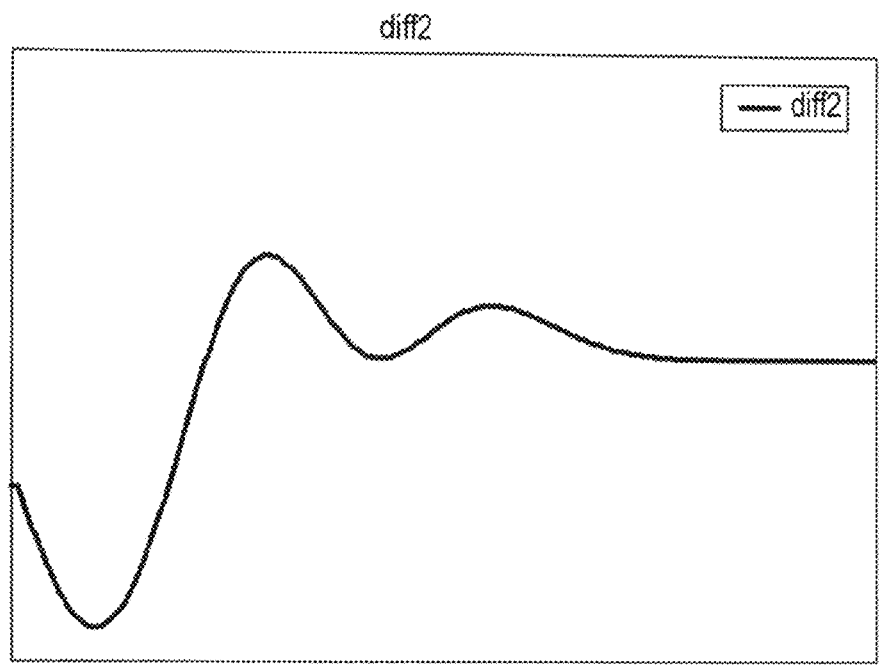
F I G. 26
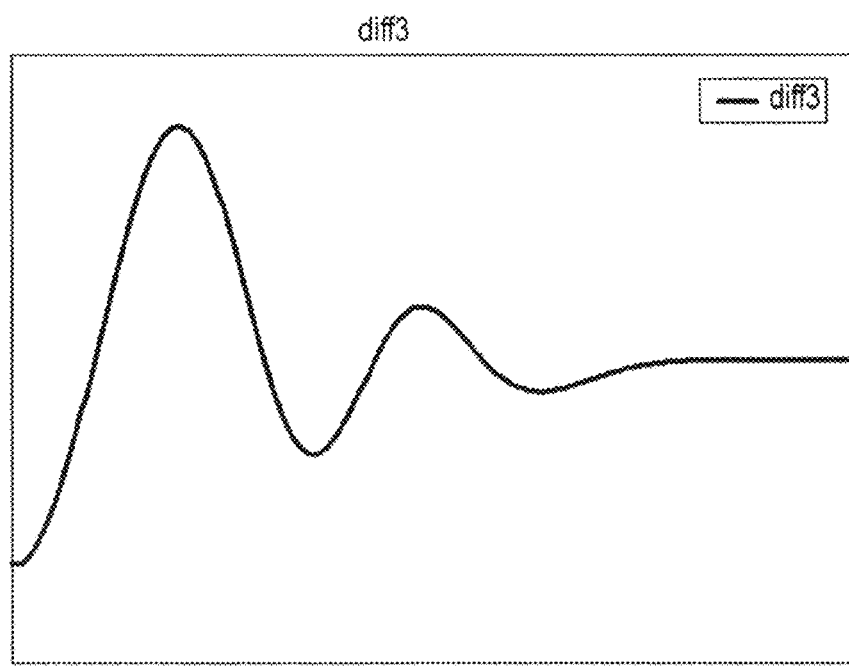
F I G. 27

ULTRASONIC DIAGNOSTIC APPARATUS, ULTRASONIC IMAGE PROCESSING APPARATUS, MEDICAL IMAGE DIAGNOSTIC APPARATUS, AND MEDICAL IMAGE PROCESSING APPARATUS

CROSS REFERENCE TO RELATED APPLICATIONS

This application is a Continuation Application of PCT Application No. PCT/JP2011/074684, filed Oct. 26, 2011 and based upon and claiming the benefit of priority from Japanese Patent Application No. 2010-240112, filed Oct. 26, 2010, the entire contents of all of which are incorporated herein by reference.

FIELD

Embodiments described herein relate generally to ultrasonic diagnostic apparatus, an ultrasonic image processing apparatus, a medical image diagnostic apparatus, and a medical image processing apparatus to be used for the purpose of performing appropriate tone correction when generating an image from a signal obtained by ultrasonic scanning using an ultrasonic probe and displaying the image.

BACKGROUND

An ultrasonic diagnostic apparatus is designed to apply ultrasonic pulses generated from vibration elements provided on an ultrasonic probe into an object and acquire biological information by receiving reflected ultrasonic waves caused by acoustic impedance differences in the tissue of the object through the vibration elements. This apparatus can display image data in real time by simple operation of bringing the ultrasonic probe into contact with the body surface. The apparatus allows to observe a moving object such as a heart and is therefore widely used for morphological diagnosis and functional diagnosis of the circulatory region and various kinds of organs. To improve the viewability of an ultrasonic image acquired by such an ultrasonic diagnostic apparatus, it is necessary to appropriately set and adjust the intensity (tone) of brightness and the like in accordance with the object.

BRIEF DESCRIPTION OF THE DRAWINGS

FIG. 1 is a block diagram showing the arrangement of an ultrasonic diagnostic apparatus 1 according to an embodiment.

FIG. 2 is a flowchart showing the procedure of each processing executed in processing according to the tone optimization function.

FIG. 3 is a flowchart showing the procedure of each processing executed in processing according to the tone optimization function.

FIG. 12 is a graph for explaining the third modification of the embodiment.

FIG. 13 is a graph for explaining the third modification of the embodiment.

FIG. 14 illustrates graphs for explaining the third modification of the embodiment.

FIG. 18 is a graph showing the second order differential equation of the histogram shown in FIG. 16.

FIG. 19 is a graph showing the third order differential equation of the histogram shown in FIG. 16.

FIG. 22 is a graph showing the second order differential equation of the histogram shown in FIG. 20.

FIG. 23 is a graph showing the third order differential equation of the histogram shown in FIG. 20.

FIG. 24 is a graph showing an example of a histogram associated with the brightness value of the ultrasonic image after gain lowering.

FIG. 25 is a graph showing the first order differential equation of the histogram shown in FIG. 24.

FIG. 26 is a graph showing the second order differential equation of the histogram shown in FIG. 24.

FIG. 27 is a graph showing the third order differential equation of the histogram shown in FIG. 24.

DETAILED DESCRIPTION

Figure 4:
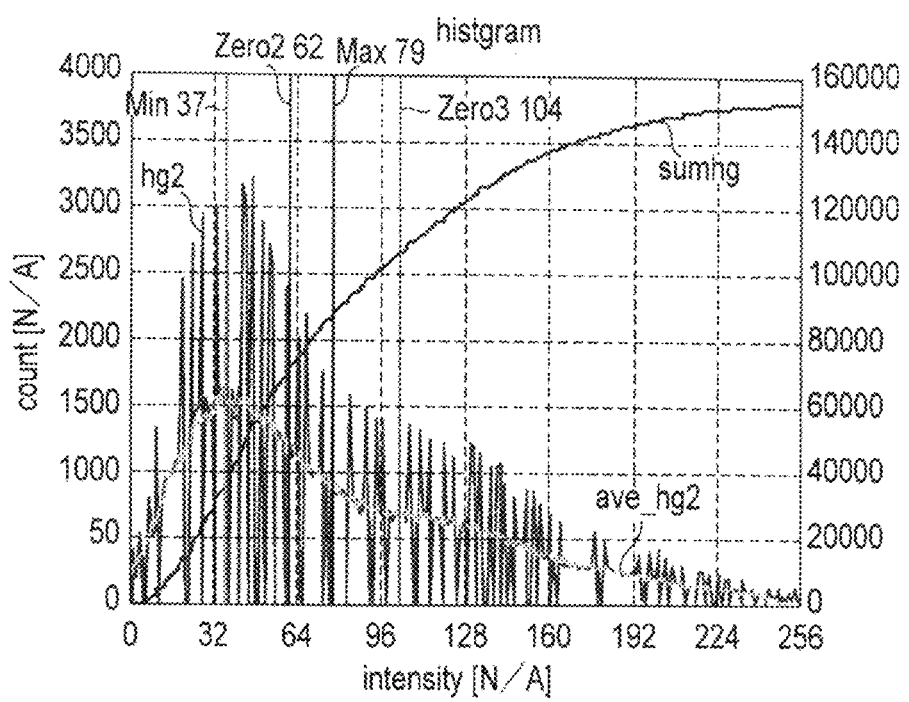
FIG. 4 is a graph showing an example of a histogram and the cumulative sum of histograms acquired in tone optimization processing.

In general, according to one embodiment, the amount of noise and the like unwanted for diagnosis increases depending on a structure or a region (organ) in a living body. This may make it difficult to do adjustment to optimize the contrast of an ultrasonic image or perform appropriate adjustment within the range adjustable by the user himself/herself. However, the conventional ultrasonic diagnostic apparatus has poor operability and, for example, in the above-described cases, cannot appropriately assist in setting/adjusting the tone of an image.

The present invention has been made in consideration of the above-described situations, and has as its object to provide an ultrasonic diagnostic apparatus, an ultrasonic image processing apparatus, a medical image diagnostic apparatus, and a medical image processing apparatus that can appropriately set/adjust the tone of an image as compared to the conventional ultrasonic diagnostic apparatus.

Solution to Problem

An ultrasonic diagnostic apparatus according to an embodiment, an ultrasonic diagnostic apparatus comprising: an image data acquisition unit configured to transmit an ultrasonic wave into a predetermined region including a diagnosis target of an object, receive a reflected wave from the predetermined region, and acquire ultrasonic image data based on the reflected wave; and a correction unit configured to execute tone correction of the ultrasonic image data, wherein in the tone correction, the correction unit calculates a histogram associated with brightness of the image data, and calculates a brightness distribution range corresponding to the diagnosis target and a tone correction function using the histogram.

Advantageous Effects of Invention

According to the present invention, it is possible to implement an ultrasonic diagnostic apparatus, an ultrasonic image processing apparatus, a medical image diagnostic apparatus, and a medical image processing apparatus that can appropriately set/adjust the tone of an image as compared to the conventional ultrasonic diagnostic apparatus.

The embodiments will now be described with reference to the accompanying drawings. Note that the same reference numerals in the following description denote constituent elements having almost the same functions and arrangements, and a repetitive description will be made only when required.

First Embodiment

FIG. 1 is block diagram showing the arrangement of an ultrasonic diagnostic apparatus 1 according to this embodiment. As shown in FIG. 1, the ultrasonic diagnostic apparatus 1 includes an ultrasonic probe 12, an input device 13, a monitor 14, an ultrasonic transmission unit 21, an ultrasonic reception unit 22, a B-mode processing unit 23, a blood flow detection unit 24, a RAW data memory 25, an image processing unit 26, a display processing unit 28 including a tone optimization unit 280, a control processor (CPU) 29, a storage unit 30, and an interface unit 31. The function of each constituent element will be described below.

The ultrasonic probe 12 is a device (probe) which transmits ultrasonic waves to an object and receives reflected waves from the object based on the transmitted ultrasonic waves. The ultrasonic probe 12 has, on its distal end, an array of a plurality of piezoelectric transducers, a matching layer, a backing member, and the like. In the ultrasonic probe 12, each of the piezoelectric transducers transmits an ultrasonic wave in a desired direction in a scan region based on a driving signal from the ultrasonic transmission unit 21 and converts a reflected wave from the object into an electrical signal. The matching layer is an intermediate layer which is provided for the piezoelectric transducers to make ultrasonic energy efficiently propagate. The backing member prevents ultrasonic waves from propagating backward from the piezoelectric transducers. When the ultrasonic probe 12 transmits an ultrasonic wave to an object P, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by the surface of a moving blood flow is subjected to a frequency shift depending on the velocity component of the moving body in the ultrasonic transmission/reception direction due to the Doppler effect.

Note that to acquire volume data, for example, a two-dimensional array probe (a probe having a plurality of ultrasonic transducers arrayed in a two-dimensional matrix) or a mechanical 4D probe (a probe which can execute ultrasonic scanning while mechanically swinging a piezoelectric transducer array in a direction perpendicular to the array direction) may be adopted as the ultrasonic probe 12. However, the ultrasonic probe to be used is not limited to these examples. For example, it is possible to use a one-dimensional array probe as the ultrasonic probe 12 and acquire volume data by performing ultrasonic scanning while manually swinging the probe.

The input device 13 is connected to an apparatus body 11 and includes various types of switches, buttons, a trackball, a mouse, and a keyboard which are used to input, to the apparatus body 11, various types of instructions, conditions, an instruction to set a region of interest (ROI), various types of image quality condition setting instructions, and the like from an operator. The input device 13 also has a start instruction, an instruction to select a target ultrasonic image, and the like for the tone optimization function (to be described later).

The monitor 14 displays morphological information and blood flow information in a living body as images based on video signals from the image processing unit 28.

The ultrasonic transmission unit 21 includes a trigger generation circuit, a delay circuit, and a pulser circuit (none of which are shown). The trigger generation circuit repetitively generates trigger pulses for the formation of transmission ultrasonic waves at a predetermined rate frequency fr Hz (period: 1/fr sec). The delay circuit gives each trigger pulse a delay time necessary to focus an ultrasonic wave into a beam and determine transmission directivity for each channel. The pulser circuit applies a driving pulse to the probe 12 at the timing based on this trigger pulse.

The ultrasonic transmission unit 21 has a function of instantly changing a transmission frequency, a transmission driving voltage, or the like to execute a predetermined scan sequence in accordance with an instruction from the control processor 28. In particular, the function of changing a transmission driving voltage is implemented by a linear amplifier type transmission circuit capable of instantly switching its value or a mechanism of electrically switching a plurality of power supply units.

The ultrasonic reception unit 22 includes an amplifier circuit, an A/D converter, and an adder (none of which are shown). The amplifier circuit amplifies an echo signal received via the probe 12 for each channel. The A/D converter gives each amplified echo signal the delay time required to determine reception directivity and perform reception dynamic focusing. The adder then performs addition processing. This addition processing will enhance a reflection component from a direction corresponding to the reception directivity of the echo signal to form a composite beam for ultrasonic transmission/reception in accordance with the reception directivity and transmission directivity.

The B-mode processing unit 23 receives an echo signal from the ultrasonic reception unit 22, and performs logarithmic amplification, envelope detection processing, and the like for the signal to generate data whose signal intensity is expressed by a brightness level.

The blood flow detection unit 24 extracts a blood flow signal from the echo signal received from the reception unit 22, and generates blood flow data. In general, CFM (Color Flow Mapping) is used for blood flow extraction. In this case, the blood flow detection unit 24 analyzes a blood flow signal to obtain an average velocity, variance, power, and the like as blood flow data at multiple points.

The RAW data memory 25 generates B-mode RAW data and blood flow RAW data for each frame using B-mode data received from the B-mode processing unit 23 and blood flow data received from the blood flow detection unit 24, respectively. The RAW data memory 25 also generates volume data from the RAW data by executing RAW/voxel conversion, as needed.

The image processing unit 28 executes scan conversion processing for the RAW data received from the RAW data memory 25. The image processing unit 28 also performs predetermined image processing such as volume rendering, multi planar reconstruction (MPR), and maximum intensity projection (MIP) for the volume data received from the RAW data memory 25. Note that for the purpose of reducing noise and improving image concatenation, it is possible to perform spatial smoothing by inserting a two-dimensional filter after the image processing unit 28.

The display processing unit 28 executes various kinds of processes associated with a dynamic range, brightness, contrast, γ curve correction, RGB conversion, and the like for various kinds of image data generated/processed by the image processing unit 28. The tone optimization unit 280 included in the display processing unit 28 executes processing corresponding to the tone optimization function (to be described later) under the control of the control processor 29.

The control processor 29 has a function as an information processing apparatus (computer), and controls the operation of this ultrasonic diagnostic apparatus. The control processor 29 reads out a dedicated program for implementing the tone optimization function (to be described later) from the storage unit 30, expands the program on the memory of its own, and executes computation/control and the like associated with various kinds of processes.

The storage unit 30 stores a dedicated program for implementing the tone optimization function (to be described later), diagnosis information (patient ID, findings by doctors, and the like), a diagnostic protocol, transmission/reception conditions, a program for implementing a speckle removal function, a body mark generation program, and other data. The storage unit is also used to store images in the RAW data memory, as needed. It is possible to transfer data in the storage unit 30 to an external peripheral device via the interface unit 31.

The interface unit 31 is an interface associated with the input device 13, a network, and a new external storage device (not shown). The interface unit 31 can transfer data such as ultrasonic images, analysis results, and the like obtained by this apparatus to another apparatus via a network.

Tone Optimization Function

The tone optimization function of the ultrasonic diagnostic apparatus 1 will be described next. This function calculates feature points from a histogram generated using individual acquired ultrasonic image data and the first and second deviations of the histogram, and sets a brightness distribution range corresponding to a diagnosis target. The function also sets control conditions using the calculated feature points, and calculates a tone correction function for each image using the set control conditions.

FIGS. 2 and 3 are flowcharts showing the procedure of each processing executed in processing (tone optimization processing) according to the tone optimization function. The contents of processing in each step will be described below.

Note that for the sake of a concrete description, tone optimization processing is assumed to be executed for an ultrasonic image acquired by ultrasonic scanning of a two-dimensional region including a cardiac muscle in the B mode. When the ultrasonic image processing apparatus implements the tone optimization processing, for example, ultrasonic image data generated in step S2 is stored in advance, and processing from step S3 is executed. In this case, the ultrasonic image processing apparatus comprises the arrangement indicated by the broken line in FIG. 1.

[Patient Information: Reception of Transmission/Reception Conditions as Inputs: Step S1]

The operator inputs patient information and selects transmission/reception conditions (the size of a region to be scanned, a focal position, a transmission voltage, and the like), an imaging mode for ultrasonic scanning on a predetermined region of an object, a scan sequence, and the like via the input device 13 (step S1). The apparatus automatically stores the input and selected various kinds of information and conditions in the storage unit 30.

[Ultrasonic Scanning: Generation of Ultrasonic Image: Steps S2 and S3]

The ultrasonic probe 12 is brought into contact with a desired position on an object surface. Ultrasonic scanning in the B mode is executed for a two-dimensional region including a diagnosis region (the heart, in this case) set as a region to be scanned (step S2). Echo signals acquired by the ultrasonic scanning in the B mode are sequentially sent to the B-mode processing unit 23 via the ultrasonic reception unit 22. The B-mode processing unit 23 executes logarithmic amplification, envelope detection processing, and the like to generate a plurality of B-mode data. The RAW data memory 25 generates B-mode RAW data using the plurality of B-mode data received from the B-mode processing unit 23. The image processing unit 26 executes scan conversion for the generated B-mode RAW data, thereby generating an ultrasonic image for each frame (step S3).

[Tone Optimization Processing: Step S4]

Next, the tone optimization unit 280 executes tone optimization processing as shown in FIG. 3 for each ultrasonic image generated by the image processing unit 26. That is, the tone optimization unit 280 first generates a histogram associated with the brightness of the ultrasonic image received from the image processing unit 26, and executes smoothing processing for the obtained histogram (step S41). After that, the tone optimization unit 280 calculates the cumulative sum of histograms, as shown in FIG. 4, and executes smoothing processing (step S42).

Figure 5:
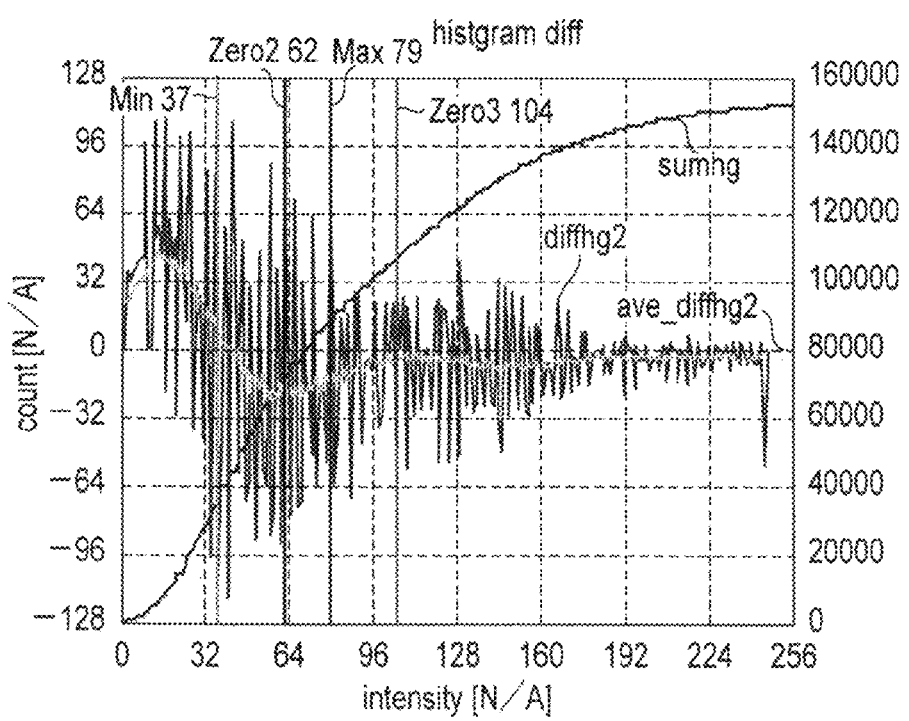
FIG. 5 is a graph showing an example of the differential of the histogram acquired in tone optimization processing.
Figure 6:
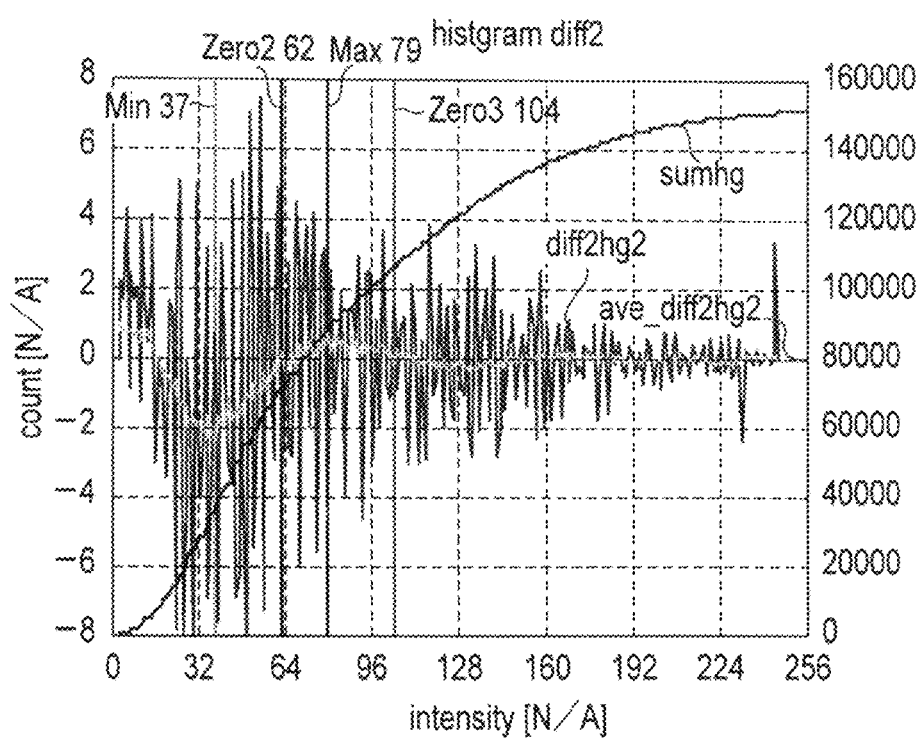
FIG. 6 is a graph showing an example of the second order differential of the histogram acquired in tone optimization processing.

The tone optimization unit 280 calculates the differential (or difference) of the histogram and then executes smoothing processing, thereby obtaining a result as shown in FIG. 5 (step S43). The tone optimization unit 280 also calculates the second order differential (or second order difference) of the histogram and then executes smoothing processing, thereby obtaining a result as shown in FIG. 6 (step S44).

Next, the tone optimization unit 280 calculates the feature points of the histogram using the calculated second order differential of the histogram (step S45). In this embodiment, as examples of the feature points of the histogram, four points are employed, that is, the negative minimum (maximal) value of the second order differential of the histogram (corresponding to the positive peak position (maximum value or maximal value) of the histogram), the second zero point of the second order differential of the histogram (the inflection point in the tail region of the histogram: corresponding to the negative peak position of the differential of the histogram), the inflection point in the tail region of the histogram, and the third zero point of the second order differential of the histogram (for example, corresponding to the branch point between the signal from the cardiac muscle region and the signal from another region).

The tone optimization unit 280 sets a brightness distribution range using the calculated feature points (step S46). For example, the tone optimization unit 280 sets a brightness distribution range L by setting a negative minimum value (maximal value) P1 of the second order differential of the histogram as the lower limit and a third zero point P4 of the second order differential of the histogram as the upper limit, as shown in FIG. 7.

The tone optimization unit 280 calculates a tone characteristic function using the calculated feature points, set control conditions, and the brightness distribution range L (step S47). For example, the tone optimization unit 280 calculates the tone characteristic function by following control conditions (1) to (5).

(1) The slope of the smoothed cumulative value at the negative minimum value (maximal value) P1 of the second order differential of the histogram is normalized to obtain the slope of the tone characteristic function.

Figure 7:
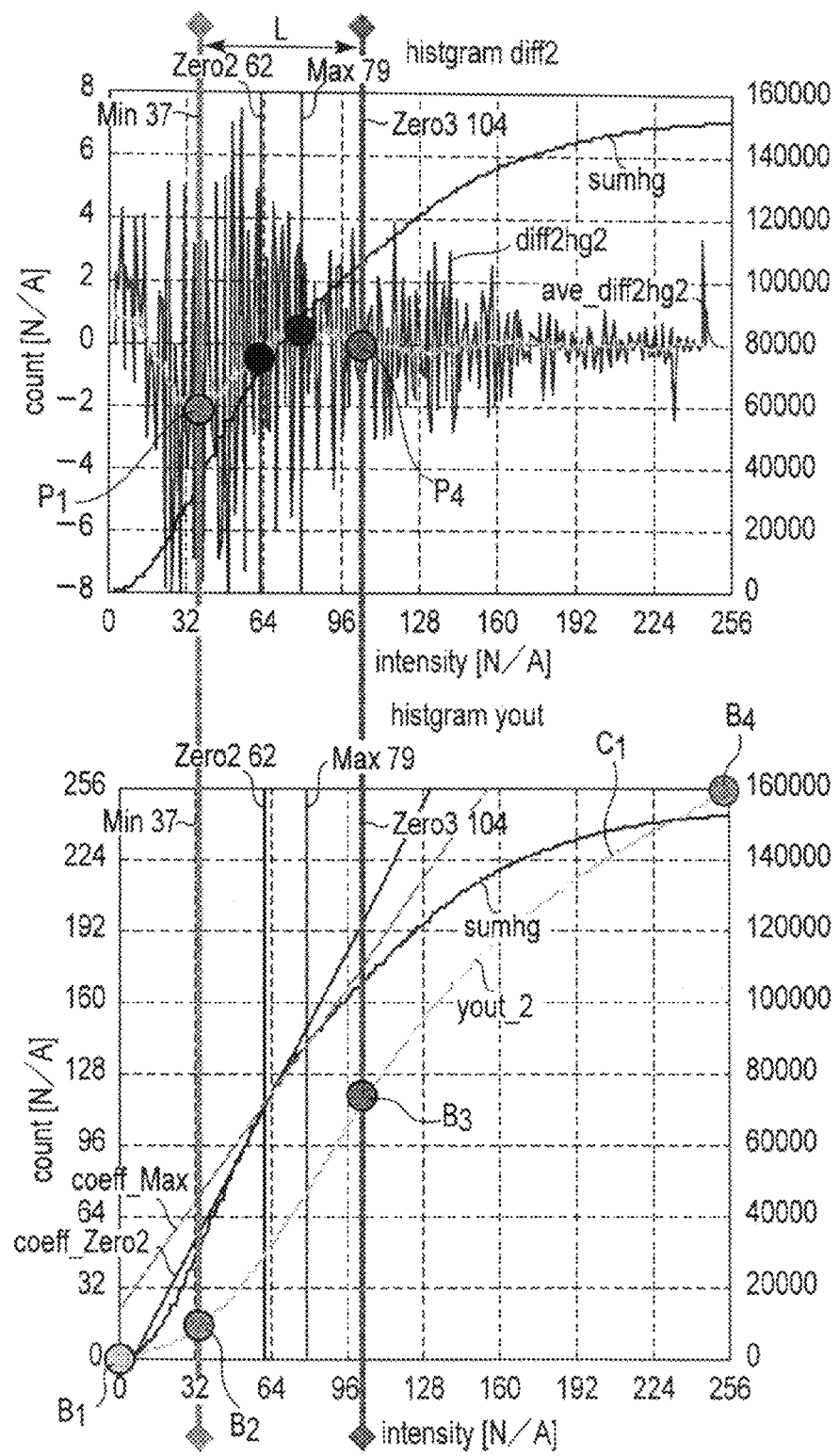
FIG. 7 illustrates graphs for explaining brightness distribution range setting processing using feature points.

(2) The input minimum value is associated with the output minimum value (a point B1 in the lower graph of FIG. 7).

(3) The upper limit of the noise level is set at the inflection point (the second zero point of the second order differential) and associated with a desired output value (a point B2 in the lower graph of FIG. 7).

(4) The object region (the cardiac muscle region, in this case) is set to the third zero point from the noise level condition (inflection point), and the output value at the third zero point is associated with a value obtained by a desired slope (a point B3 in the lower graph of FIG. 7).

(5) The input maximum value is associated with the output maximum value (a point B4 in the lower graph of FIG. 7).

The tone optimization unit 280 calculates, for example, a tone correction function C1 in the lower graph of FIG. 7 by interpolating (for example, spline interpolation) the tone characteristic function obtained in step S47 (step S48). Tone optimization processing is executed for the ultrasonic image using the calculated tone correction function C1 (step S49).

[Display of Ultrasonic Image: Step S5]

Next, the monitor 14 displays, in a desired format, the ultrasonic image that has undergone the tone optimization processing (step S5).

Figure 8:
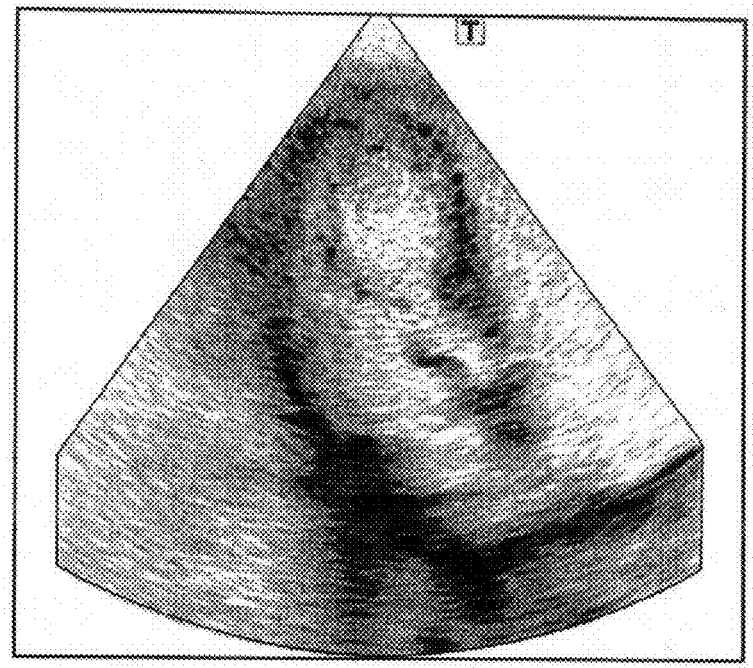
FIG. 8 is a view showing an example of an ultrasonic image that has not undergone tone optimization processing.
Figure 9:
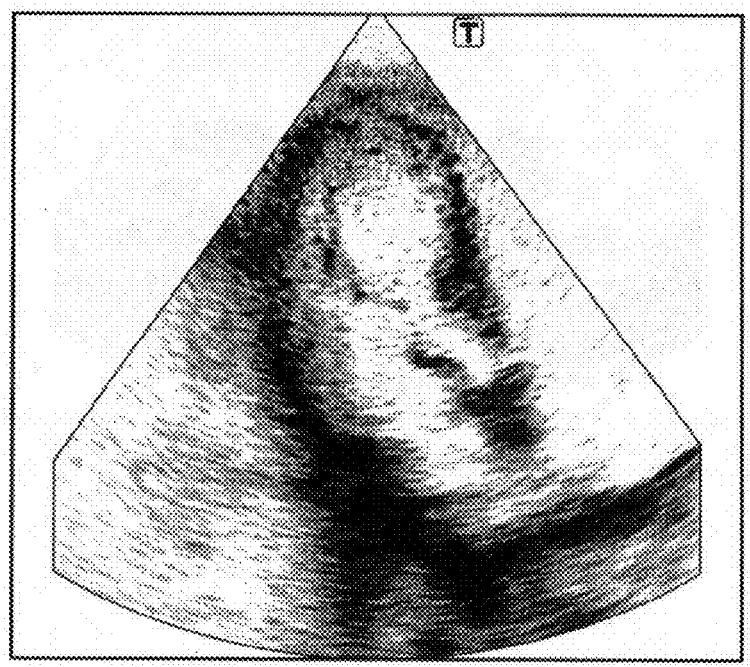
FIG. 9 is a view showing an example of an ultrasonic image obtained by performing tone optimization processing for the image in FIG. 8.

FIG. 8 is a view showing an example of an ultrasonic image that has not undergone the tone optimization processing. FIG. 9 is a view showing an example of an ultrasonic image obtained by performing the tone optimization processing for the image in FIG. 8. As is apparent from comparison between FIGS. 8 and 9, the ultrasonic image whose tone has been adjusted by the tone optimization processing has a clearer contrast and is easy to see.

Note that the contents of the tone optimization processing are not limited to those described above. Modifications of the tone optimization processing will be explained below.

First Modification

Figure 10:
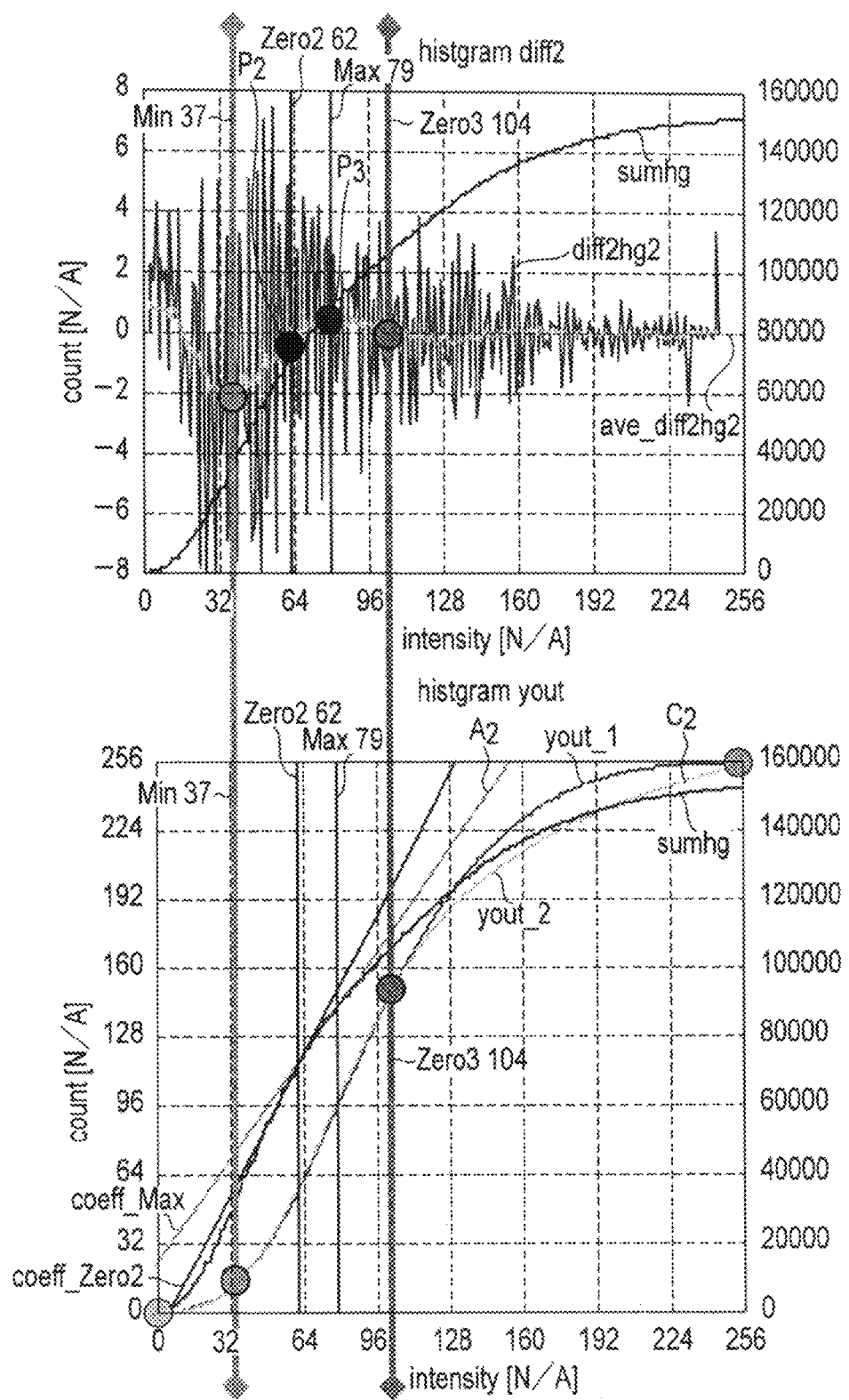
FIG. 10 illustrates graphs showing a modification that adopts the slope of A2 calculated by normalizing the slope of the smoothed cumulative value at a second zero point P2.

For example, as shown in FIG. 10, a tone correction function C2 can be calculated by adopting the slope of A2 calculated by normalizing the slope of the smoothed cumulative value at a second zero point P2. A slope calculated by averaging the slopes within the range (for example, the brightness distribution range P2-P3) corresponding to the object region may be adopted.

Second Modification

The tone characteristic function may be calculated by adding another control condition to the above-described conditions (1) to (5). For example, it is possible to add the following condition aiming at suppressing the slope of the high brightness region.

Figure 11:
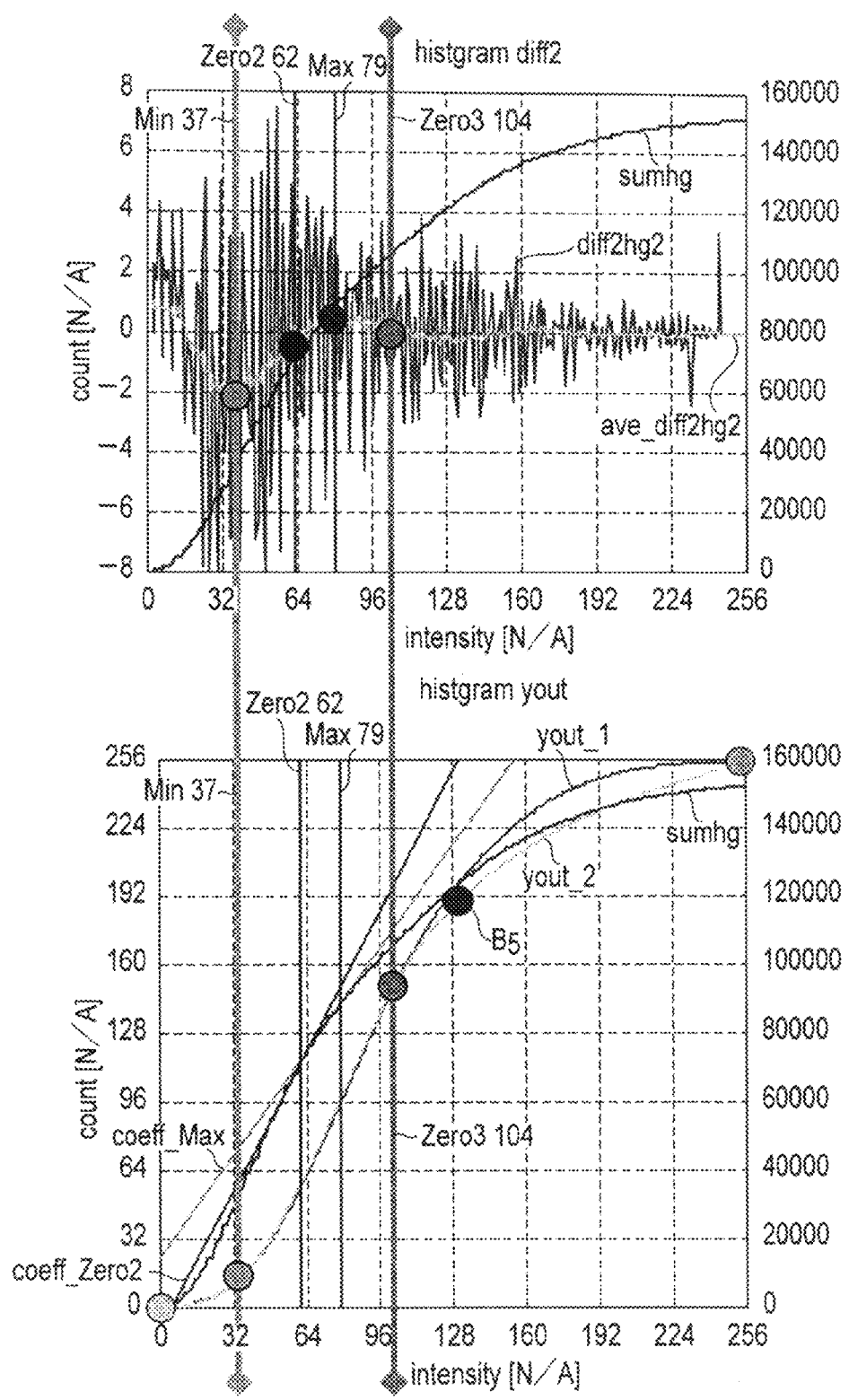
FIG. 11 illustrates graphs for explaining the second modification of the embodiment.

(6) An input value that exists from the third zero point to the input maximum value (for example, a tone of 256) is selected and associated with a desired output value (for example, a point B5 in the lower graph of FIG. 11).

Note that the control condition (6) may parallelly be added to the control conditions (1) to (5) when calculating the tone characteristic function. The tone characteristic function may newly be calculated by adding the control condition (6) as needed in consideration of the result of the tone characteristic function calculated using the control conditions (1) to (5). If the tone characteristic at the position corresponding to the added control condition is less than, for example, 255, correction is preferably done to make the tone characteristic function monotonically increase so as to suppress the fluctuations in the characteristic.

Third Modification

Tone expansion processing may be performed as needed. Whether to do tone expansion processing is determined in, for example, the following way. If the cumulative sum of histograms of the input image reaches a predetermined amount before the end processing region of smoothing, it is determined that the dynamic range (DR) or tone characteristic at the time of image acquisition is not appropriate. Hence, the tone characteristic is expanded, as shown in FIGS. 12 and 13, in, for example, calculation of step S47.

Fourth Modification

The brightness distribution range can arbitrarily be changed. For example, the above-described brightness distribution range L (lower limit: the negative minimum value of the second order differential of the histogram, upper limit: third zero point) in FIG. 7 can be changed to a brightness distribution range L1 (lower limit: second zero point, upper limit: third zero point) shown in FIG. 14 at an arbitrary timing. This may enable to more suitably extract the object.

Fifth Modification

The tone optimization processing is also applicable to a case in which a moving image is acquired and displayed.

Figure 15:
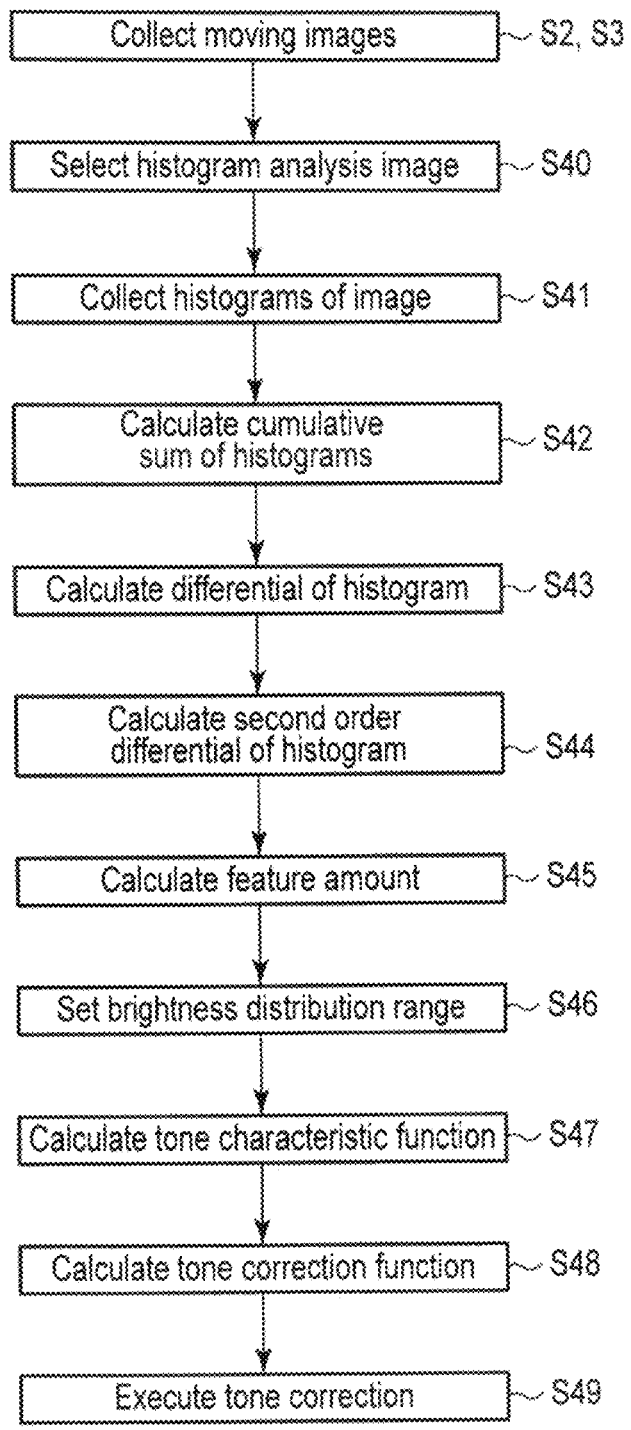
FIG. 15 is a flowchart showing the procedure when the tone optimization processing is applied to moving image display (the case of the fifth modification).

FIG. 15 is an example of a flowchart when the tone optimization processing is applied to moving image display. As compared to the flowchart shown in FIG. 3, "histogram analysis image selection processing" of step S40 is added.

In the histogram analysis image selection processing (step S40), one of a plurality of acquired ultrasonic images (for example, ultrasonic images of a heart for one or a plurality of heartbeats) is selected, and the tone optimization processing from step S41 is then executed. As the histogram analysis image, for example, an image corresponding to a preset phase or timing, an image corresponding to the start, middle, or end phase of a predetermined period, an image having a maximum average brightness, an image whose average brightness is average in a plurality of images, or the like can be selected. Which image is to be selected as the histogram analysis image can freely be set. If the diagnosis target is the heart, selecting a totally dark image or an image that has not appropriately visualized the object should be prohibited because the cumulative sum of histograms periodically varies in accordance with the dilatation/contraction.

Sixth Modification

The tone optimization processing can be executed, for example, every time ultrasonic image data is acquired. If the processing need not always be executed for all images, it may be executed at an arbitrary timing in response to, for example, an instruction input by the user via the input device 13.

Application Example

In the above-described embodiment, an example has been explained in which the first extreme value, the second and third zero points, and the like of the second order differential equation of the histogram associated with the brightness value of an ultrasonic image are calculated as feature points. However, the tone optimization function is not limited to this example. For example, the ith extreme value and the jth zero point of the nth order differential equation (n, i, and j are arbitrary natural numbers) may be calculated as feature points, and the brightness distribution range and the tone correction curve may be calculated using the obtained feature points.

According to the above-described arrangement, the following effects can be obtained.

According to the ultrasonic diagnostic apparatus, feature points are calculated from a histogram generated using acquired ultrasonic image data and the first order differential, the second order differential, and the like of the histogram, and the brightness distribution range corresponding to the diagnosis target is set. Control conditions are set using the calculated feature points, and the tone correction function is calculated using the set control conditions. This allows to define appropriate brightness distribution range and tone correction function corresponding to the tone characteristic of an individual image. It is consequently possible to quickly and easily optimize tone correction in accordance with the diagnosis target, individual differences, and imaging situation.

Second Embodiment

An ultrasonic diagnostic apparatus according to the second embodiment will be described next. When gain adjustment is performed for an ultrasonic image that is the target of tone optimization processing, the shape of the histogram associated with the brightness value after the gain adjustment changes. As a result, the cumulative sum of histograms and the shape of the nth order differential equation (n is a natural number) also change. In this embodiment, tone optimization processing when the histogram shape has changed due to gain adjustment will be described.

Figure 16:
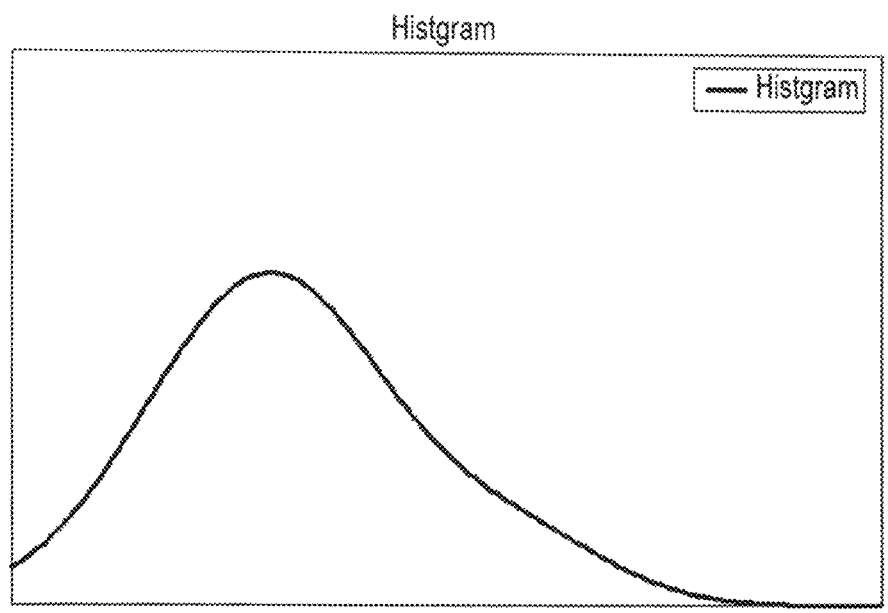
FIG. 16 is a graph showing an example of a histogram associated with the brightness value of a predetermined ultrasonic image before gain adjustment.
Figure 17:
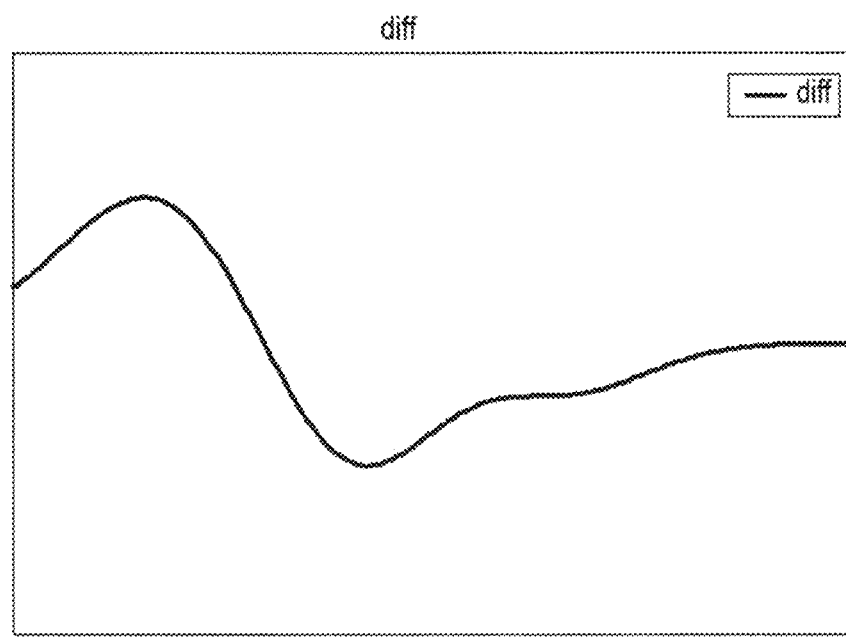
FIG. 17 is a graph showing the first order differential equation of the histogram shown in FIG. 16.
Figure 20:
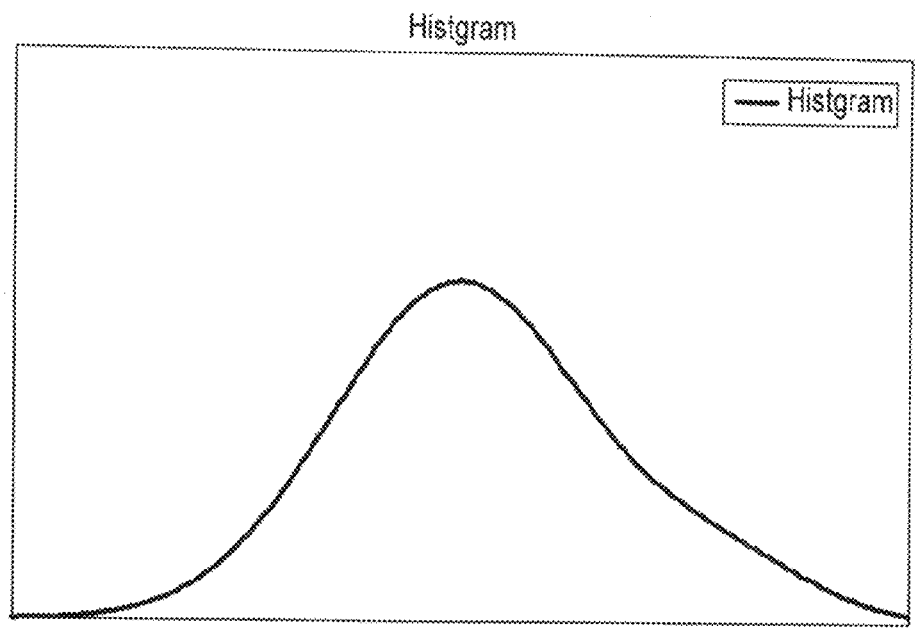
FIG. 20 is a graph showing an example of a histogram associated with the brightness value of the ultrasonic image after gain raising.
Figure 21:
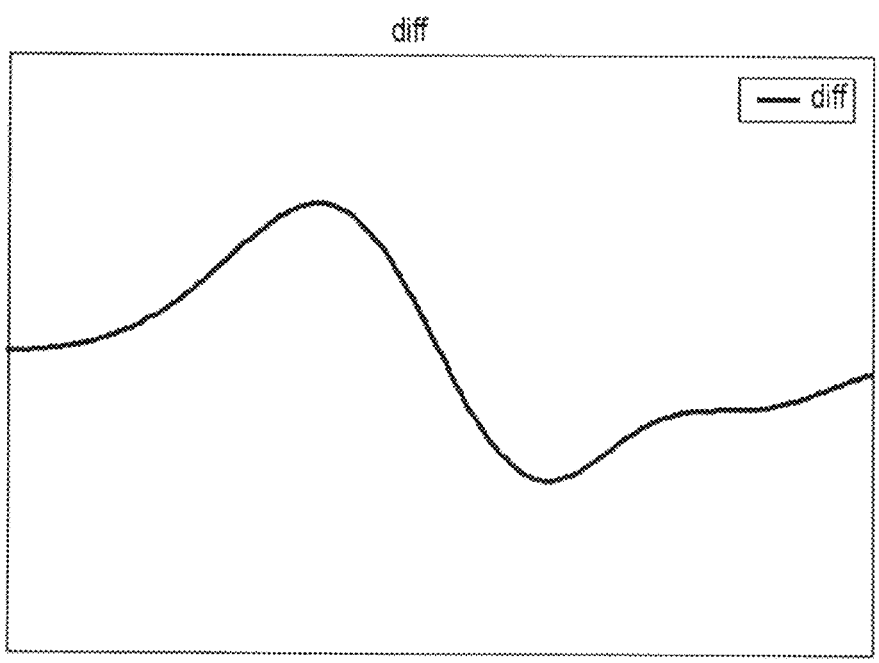
FIG. 21 is a graph showing the first order differential equation of the histogram shown in FIG. 20.

Assume that a predetermined ultrasonic image is acquired, and a histogram associated with the brightness value of the image before gain adjustment is obtained as shown in FIG. 16. In this case, the first order differential equation, the second order differential equation, and the third order differential equation of the histogram are obtained as shown in FIGS. 17, 18, and 19, respectively.

When processing of raising the gain is performed for the current ultrasonic image (the ultrasonic image corresponding to the histogram in FIG. 16), the histogram associated with the brightness value and the first order differential equation, the second order differential equation, and the third order differential equation of the histogram after gain raising are obtained as shown in FIGS. 20, 21, 22, and 23, respectively. For example, comparing FIG. 16 with FIG. 20 reveals that the peak position of the histogram has moved (shifted to right) upon gain raising. Comparing FIG. 17 with FIG. 21, FIG. 18 with FIG. 22, and FIG. 19 with FIG. 23 reveals that the position of each extreme value and that of each zero point have also moved (shifted to right) in each order differential equation upon gain raising. Especially, referring to FIGS. 19 and 23, the polarity of the extreme value that appears for the first time in FIG. 19 is negative, whereas the polarity of the extreme value that appears for the first time in FIG. 23 is positive. Hence, for example, the condition "the first and second extreme values of the third order differential equation shown in FIG. 19 are adopted as feature points" corresponds to the condition "the second and third extreme values of the third order differential equation before gain adjustment shown in FIG. 23 are adopted as feature points".

When processing of lowering the gain is performed for the current ultrasonic image, the histogram associated with the brightness value and the first order differential equation, the second order differential equation, and the third order differential equation of the histogram after gain lowering are obtained as shown in FIGS. 24, 25, 26, and 27, respectively. For example, comparing FIG. 16 with FIG. 24 reveals that the peak position of the histogram has shifted to left upon gain lowering. Comparing FIG. 17 with FIG. 25, FIG. 18 with FIG. 26, and FIG. 19 with FIG. 27 reveals that the position of each extreme value and that of each zero point have also shifted to left in each order differential equation upon gain lowering. Especially, comparing the first order differential equation, the second order differential equation, and the third order differential equation before gain raising with those after gain raising reveals that the polarity of the extreme value of the same order is inverted (for example, the polarity of the first extreme value of the first order differential equation before gain raising is positive, whereas the polarity of the first extreme value after gain raising is negative). Hence, for example, the condition "the second and third zero points of the second order differential equation shown in FIG. 18 are adopted as feature points" corresponds to the condition "the first and second extreme values of the second order differential equation before gain adjustment shown in FIG. 26 are adopted as feature points".

That is, the peak position of a histogram, and the polarity of each extreme value and the position of each zero point in the nth order differential equation of the histogram change upon gain adjustment. Hence, the ith extreme value and the jth zero point (i and j are natural numbers) to be used to calculate feature points in tone optimization processing are preferably appropriately selected individually in accordance with the positions and shapes of the histogram and the nth order differential equation after gain correction.

Note that the present invention is not limited to each embodiment described above, and constituent elements can be modified and embodied in the execution stage within the spirit and scope of the invention. The followings are concrete modifications.

(1) Each function associated with each embodiment can also be implemented by installing programs for executing the corresponding processing in a computer such as a workstation and expanding them on a memory. In this case, the programs which can cause the computer to execute the corresponding techniques can be distributed by being stored in recording media such as magnetic disks ((floppy®) disks, hard disks, and the like), optical disks (CD-ROMs, DVDs, and the like), and semiconductor memories.

(2) In the above embodiments, an example has been described in which tone optimization processing is performed for an ultrasonic image acquired by ultrasonic scanning of a two-dimensional region including a cardiac muscle in the B mode. However, the tone optimization function is not limited to this example. The function is also applicable to, for example, a case in which a part other than the heart is the diagnosis target, a case in which imaging is performed not in the B mode but in a blood flow detection mode (CFM mode or the like), a case in which ultrasonic scanning of a three-dimensional region is performed, and the like. Especially in ultrasonic scanning of a three-dimensional region, suitable ultrasonic images can be acquired by applying the tone optimization processing to the two-dimensional images and MPR images included in volume data.

(3) The above embodiments have exemplified the case in which the tone optimization processing is executed for ultrasonic image data acquired by the ultrasonic diagnostic apparatus. However, the tone optimization processing is applicable not only to ultrasonic image data but also to a medical image acquired by a medical image diagnostic apparatus such as an X-ray diagnostic apparatus, an X-ray computed tomography apparatus, or a magnetic resonance imaging apparatus. The tone optimization processing may be performed ex post facto using a medical image processing apparatus for images acquired by various kinds of medical image diagnostic apparatuses.

Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
    an ultrasonic probe configured to transmit an ultrasonic wave into a predetermined region including a diagnosis target of an object, receive a reflected wave from the predetermined region, and convert the reflected wave into an electrical signal; and
    processing circuitry configured to
        acquire ultrasonic image data based on the electrical signal, and
        execute tone correction on the ultrasonic image data, wherein, in the tone correction, the processing circuitry calculates a histogram associated with brightness of the ultrasonic image data, and calculates a brightness distribution range corresponding to the diagnosis target and a tone correction function using the histogram, wherein the processing circuitry calculates the brightness distribution range and the tone correction function using at least one feature point, which is obtained from a second order differential of the histogram.

2. The ultrasonic diagnostic apparatus according to claim 1, wherein the processing circuitry
    calculates a cumulative sum of the histograms, and
    calculates a slope of the tone correction function using a slope of the cumulative sum within the brightness distribution range.

3. The ultrasonic diagnostic apparatus according to claim 1, wherein the processing circuitry calculates the brightness distribution range and the tone correction function using an inflection point of the histogram as one of the feature points.

4. The ultrasonic diagnostic apparatus according to claim 1, wherein the processing circuitry calculates the tone correction function using at least one of a minimum value, a maximum value, a second zero point, and a third zero point of the second order differential of the histogram as one of the feature points.

5. The ultrasonic diagnostic apparatus according to claim 1, wherein the processing circuitry calculates the tone correction function using an arbitrary point designated via a computer interface as one of the feature points.

6. The ultrasonic diagnostic apparatus according to claim 1, wherein the tone correction includes performing gain adjustment, and when the gain adjustment is performed by the processing circuitry, the processing circuitry calculates the histogram associated with the brightness of the ultrasonic image data after the gain adjustment.

7. The ultrasonic diagnostic apparatus according to claim 1, wherein
    the diagnosis target is a heart, and
    the processing circuitry determines a region of the histogram corresponding to a cardiac muscle as the brightness distribution range.

8. The ultrasonic diagnostic apparatus according to claim 1, further comprising a computer interface configured to input a start instruction of the tone correction,
    wherein the processing circuitry executes the tone correction in response to the start instruction input via the computer interface.

9. The ultrasonic diagnostic apparatus according to claim 1, wherein the processing circuitry executes the tone correction every time the processing circuitry acquires the ultrasonic image data.

10. The ultrasonic diagnostic apparatus according to claim 1, wherein the processing circuitry calculates the brightness distribution range and the tone correction function using at least one of the feature points, which are obtained from an nth order differential (n is a natural number) of the histogram.

11. The ultrasonic diagnostic apparatus according to claim 10, wherein the processing circuitry calculates the brightness distribution range and the tone correction function using an inflection point of the histogram as one of the feature points.

12. The ultrasonic diagnostic apparatus according to claim 10, wherein the processing circuitry calculates the tone correction function using at least one of an ith extreme value and a jth zero point of an nth order differential (n, i, and j are natural numbers) of the histogram as one of the feature points.

13. The ultrasonic diagnostic apparatus according to claim 10, wherein the processing circuitry calculates the tone correction function using an arbitrary point designated via a computer interface as one of the feature points.

14. An ultrasonic image processing apparatus comprising:
memory circuitry storing ultrasonic image data associated with a predetermined region including a diagnosis target of an object;
processing circuitry configured to execute tone correction on the ultrasonic image data; and
a display configured to display an ultrasonic image obtained by executing the tone correction on the ultrasonic image data,
wherein, in the tone correction, the processing circuitry
calculates a histogram associated with brightness of the ultrasonic image data,
calculates a brightness distribution range corresponding to the diagnosis target and a tone correction function using the histogram, and
calculates the brightness distribution range and the tone correction function at least one feature point, which is obtained from a second order differential of the histogram.

15. The ultrasonic image processing apparatus according to claim 14, wherein the processing circuitry
calculates a cumulative sum of the histograms, and
calculates a slope of the tone correction function using a slope of the cumulative sum within the brightness distribution range.

16. The ultrasonic image processing apparatus according to claim 14, wherein the processing circuitry calculates the brightness distribution range and the tone correction function using an inflection point of the histogram as one of the feature points.

17. The ultrasonic image processing apparatus according to claim 14, wherein the processing circuitry calculates the tone correction function using at least one of a minimum value, a maximum value, a second zero point, and a third zero point of the second order differential of the histogram as one of the feature points.

18. The ultrasonic image processing apparatus according to claim 14, wherein the processing circuitry calculates the tone correction function using an arbitrary point designated via a computer interface as one of the feature points.

19. The ultrasonic image processing apparatus according to claim 14, wherein
the diagnosis target is a heart, and
the processing circuitry determines a region of the histogram corresponding to a cardiac muscle as the brightness distribution range.

20. The ultrasonic image processing apparatus according to claim 14, further comprising a computer interface configured to input a start instruction of the tone correction,
wherein the processing circuitry executes the tone correction in response to the start instruction input via the computer interface.

21. The ultrasonic image processing apparatus according to claim 14, wherein the processing circuitry executes the tone correction every time the memory circuitry stores the ultrasonic image data.

22. The ultrasonic image processing apparatus according to claim 14, wherein the tone correction includes performing gain adjustment, and when the gain adjustment is performed by the processing circuitry, the processing circuitry calculates the histogram associated with the brightness of the ultrasonic image data after the gain adjustment.

23. The ultrasonic image processing apparatus according to claim 14, wherein the processing circuitry calculates the brightness distribution range and the tone correction function using at least one of the feature points, which are obtained from an nth order differential (n is a natural number) of the histogram.

24. The ultrasonic image processing apparatus according to claim 23, wherein the processing circuitry calculates the brightness distribution range and the tone correction function using an inflection point of the histogram as one of the feature points.

25. The ultrasonic image processing apparatus according to claim 23, wherein the processing circuitry calculates the tone correction function using at least one of an ith extreme value and a jth zero point of an nth order differential (n, i, and j are natural numbers) of the histogram as one of the feature points.

26. The ultrasonic image processing apparatus according to claim 23, wherein the processing circuitry calculates the tone correction function using an arbitrary point designated via input interface circuitry as one of the feature points.

27. A medical image diagnostic apparatus, comprising:
processing circuitry configured to
acquire image data associated with a predetermined region including a diagnosis target of an object; and
execute tone correction on the image data, wherein, in the tone correction, the processing circuitry calculates a histogram associated with brightness of the image data, and calculates a brightness distribution range corresponding to the diagnosis target and a tone correction function using the histogram, wherein the processing circuitry calculates the brightness distribution range and the tone correction function using at least one feature point, which is obtained from a second order differential of the histogram.

28. A medical image processing apparatus, comprising:
memory circuitry storing image data associated with a predetermined region including a diagnosis target of an object;
processing circuitry configured to execute tone correction on the image data; and
a display configured to display an image obtained by executing the tone correction on the image data,
wherein, in the tone correction, the processing circuitry calculates a histogram associated with brightness of the image data, and calculates a brightness distribution range corresponding to the diagnosis target and a tone correction function using the histogram, wherein the processing circuitry calculates the brightness distribution range and the tone correction function using at least one feature point, which is obtained from a second order differential of the histogram.

* * * * *